United States Patent [19]

Sato et al.

[11] Patent Number: 4,528,034
[45] Date of Patent: Jul. 9, 1985

[54] SELENIUM-CONTAINING AMALGAM ALLOYS FOR DENTAL RESTORATION AND METHOD FOR THE PREPARATION THEREOF

[75] Inventors: Atsushige Sato; Ishi Miura; Yasuhiro Kumei, all of Tokyo; Osamu Okuno, Narashino; Tsuyoshi Nakano, Chiba; Bunsaku Yoshida, Warabi, all of Japan

[73] Assignees: Atsushige Sato; Ishi Miura; G-C Dental Industrial Corp., all of Tokyo, Japan

[21] Appl. No.: 478,498

[22] Filed: Mar. 24, 1983

[30] Foreign Application Priority Data

Apr. 2, 1982 [JP] Japan .................................. 57-53681

[51] Int. Cl.$^3$ ................................................ C22C 5/08
[52] U.S. Cl. ..................................... 75/255; 420/527; 420/502; 420/503; 420/504
[58] Field of Search ............... 420/501, 503, 502, 504, 420/526, 506, 587, 527, 580; 75/251, 255

[56] References Cited

U.S. PATENT DOCUMENTS 4,008,073 2/1977 Kropp ................................. 75/0.5 R
4,385,892 5/1983 Sato et al. ........................... 433/228

Primary Examiner—Melvyn J. Andrews
Assistant Examiner—Christopher W. Brody
Attorney, Agent, or Firm—Oblon, Fisher, Spivak, McClelland & Maier

[57] ABSTRACT

Selenium-containing amalgam alloys for dental restoration comprises 0.1–50% by weight of any one of the following alloy powders (A), (B) and (C) mixed with 50–99.9% by weight of the following amalgam alloy powders (D).

(A): Silver alloy powders containing no less than 50% by weight of silver and 0.01–10% by weight of selenium, (B): Copper alloy powders containing no less than 50% by weight of copper and 0.01–5% by weight of selenium, (C): Alloy powders mix of (A) with (B) wherein the total amount of silver and copper is adjusted to no less than 50% by weight, and the amount of selenium to 0.01–10% by weight, and (D): Silver-tin-copper amalgam alloy powders. At least one of the any one of (A), (B) and (C) and (D) may be pre-amalgamated with mercury in an amount of no higher than 3% by weight based on the total weight thereof.

4 Claims, No Drawings

SELENIUM-CONTAINING AMALGAM ALLOYS FOR DENTAL RESTORATION AND METHOD FOR THE PREPARATION THEREOF

FIELD OF THE INVENTION

The present invention relates to selenium-containing amalgam alloys for dental restoration and a method for the preparation thereof.

BACKGROUND OF THE INVENTION

Dental amalgams are a blend or admixture which consists essentially of silver, tin and copper with the balance being mercury, and is filled and set in cavities in the teeth in the mouth.

As stipulated in JIS T 6109, the known dental amalgam alloys enjoying wide use until now are generally composed of, on the weight basis, 65% or higher of silver, 29% or less of tin, 6% or less of copper, 3% or less of mercury and 2% or less of zinc. However, the alloys complying with that standard have been found to be unsatisfactory as regards their mechanical properties and corrosion resistance due to the fact that the ($\gamma_2$) phase of $Sn_{7-8}Hg$ crystallized out in the set amalgams is poor in strength and corrosion.

As the amalgam alloys in which no crystallization of that ($\gamma_2$) phase takes place, the so-called high-copper type amalgam alloys have recently been introduced, including those referred to as the so-called dispersion-strengthened type. Such alloys are characterized by their increased copper content that exceeds the value provided by the Japanese Industrial Standards (JIS). This feature suppresses crystallization of the ($\gamma_2$) phase and, instead, effect crystallization of the ($\epsilon$) phase and ($\eta$) phase of $Cu_3Sn$ and $Cu_6Sn_5$ which contribute to improvements in mechanical properties.

With the known amalgam alloys as mentioned above, however, no care is taken of changes in the compressive strength in the initial packing stage (hereinafter referred to as the initial compressive strength) and of the toxicity to cells of the mercury leaching out of amalgam slurries. That is to say, a time period of several hours is required until the packed amalgam reaches a strength capable of resisting to initial biting forces. During this period, the packed amalgam may possibly be broken by external forces such as biting forces. In addition, when amalgam filling come in contact with the oral fluids in the course of time during which the amalgam sets sufficiently, the mercury leaches out of the amalgam slurry, and may accumulate inside the body.

SUMMARY OF THE INVENTION

According to one feature of the present invention, it has been found that selenium can be an element that is effective both for increasing the initial compressive strength of dental amalgams for the purpose of reducing the possibilities of breaking them due to the initial biting forces and for eliminating the toxicity to cells of the mercury leaching out of amalgams slurries and coming into contact with the oral fluids.

Thus, the present invention provides the novel selenium-containing amalgam alloys which comprises 0.1–50% by weight of any one of the following alloy powders (A), (B) and (C) mixed with 50–99.9% by weight of the following amalgam ally powders (D).

(A): Silver alloy powders containing no less than 50% by weight of silver and 0.01–10% by weight of selenium, (B): Copper alloy powders containing no less than 50% by weight of copper and 0.01–5% by weight of selenium, (C) Alloy powders mix of (A) with (B) wherein the total amount of silver and copper is adjusted to no less than 50% by weight, and the amount of selenium to 0.01–10% by weight, and (D): Silver-tin-copper amalgam alloy powders.

PREFERRED EMBODIMENTS OF THE INVENTION

As well-known in the art, the amalgams have their mechanical properties affected by the functions of various $\gamma_2$, $\epsilon$ and $\eta$ phases formed therein. When selenium is present, however, its part reacts with silver to yield a SeHg phase in addition to the said various phases found in the conventional amalgams. That SeHg phase forms just after triturating alloy and mercury, and has an influence on both a lowering of the plasticity of an amalgam slurry, which contributes to increasing the initial compressive strength, and improvements in the mechanical properties of the set amalgam, such as its final compressive strength or flow.

In particular, the alloying of selenium in the form of an eutectic crystal with one or more metallic elements selected from the group consisting of silver, copper, gold, nickel, cobalt, tin, indium, palladium, antimony, germanium and the like, has been found to be most effective, since the formed SeHg phase is divided more finely than obtained with the addition of selenium powder alone.

Preferably, the selenium-containing silver and copper alloys according to the present invention have a selenium content of 0.01–10% and 0.01–5%, respectively.

According to the present invention, the most unique feature of selenium is that it resists antagonistically to the toxicity to cells of the mercury leaching from an amalgam slurry into the oral fluids.

The threshold solubility of selenium with respect to silver and copper is about 9% and 3–4%, respectively. Thus, there can be a variation of the alloy limit when one or more of metallic elements from gold, nickel, cobalt, tin, indium, palladium, antimony and germanium, exclusive of silver and copper, exist. For this reason, the compressive strength of the set amalgam decreases when selenium is present in an amount exceeding the critical value. This is the reason why the upper limits of selenium are fixed at 10% and 5%, respectively, for the silver and copper alloys.

With an alloy mix consisting of a silver alloy and a copper alloy, the upper limit of its selenium content is also fixed at 10% for the reasons as mentioned above.

The lower limit of a selenium content in either the silver alloy or the copper alloy is 0.01% since, below that value, selenium does not give any effect to both the mechanical properties of the set amalgam and the elimination of the toxicity to cells.

It is understood that the terms "silver alloy" and "copper alloy" refer to the alloys containing as the main component no less than 50% of silver and copper, respectively.

The selenium-containing silver and/or copper alloys should preferably be mixed with the silver-tin-copper amalgam alloys composed mainly of silver, tin and copper in an amount of 0.1–50%.

In general, when the amount of the silver and/or copper alloy exceeds 50%, an amalgam-mercury slurry sets so rapidly that clinical difficulties are encountered in packing the amalgam. This is the reason why the maximum amount of the selenium-containing alloy is fixed at 50%. On the other hand, the reason for fixing the minimum amount of the selenium-containg alloy is that, below that value, no appreciative effect is obtained.

As the silver-tin-copper amalgam alloys to be mixed with the selenium-containing silver and/or copper alloys, the foregoing high-copper type alloys inclusive of the foregoing dispersion-strengthened type alloys, in addition to any alloy meeting the Japanese Industrial Standards, may be used with equivalent results.

The selenium-containing silver and/or copper alloys as well as the silver-tin-copper amalgam alloys mixed therewith may be powdered to any desired shape such as a spherical or lathe cut particle. In any cases, similar results are obtained.

The so-called preamalgamation treatment may be applied to the present invention, in which mercury is treated onto the surface of amalgam alloy particles to amalgamate one surface layer, which improves the compatibility of the particles to fresh mercury when mixing them together. However, the foregoing JIS T 6109 provides that the amalgam alloys should have a mercury content of no more than 3%. Indeed, the preamalgamation of the particles' surface alone with a minor amount of mercury improves the watability threrof to mercury, but tends to delay setting. It is thus recommendable that the upper limit of mercury is fixed at 3 % based on the total weight of amalgam particles, taking into consideration the thickness of the layer to be preamalgamated. The preamalgamation with mercury may advantageously be applied to at least one of the selenium-containing silver and/or copper alloy powders and the silver-tin-copper amalgam alloy powders.

Zinc acts effectively as a deacidification agent during the preparation of alloys, reacts vigorously with mercury, and promotes amalgamation in an increased amount. For allowance of a manipulation time, it is thus preferable to apply zinc in an amount up to 2%. The foregoing JIS T 6109 provides that the use of zinc in an amount of up to 2% is acceptable, and the ordinary amalgam alloys are prepared within the zinc range as mentioned above. Thus, the critical upper limit of zinc is also preferably fixed at 2% in the present invention.

The present invention also relates to a method for the preparation of the novel selenium-containing dental amalgam alloys according to the present invention. Thus, the method accoding to the invention comprises the steps of melting any one of the following alloys (A), (B) and (C), reducing the resulting melt to powders having a desired particle size by spraying the melt with or without treatments wherein it is solidified and, then, remelted, in an inert gas stream by means of a nozzle, a centrifugal force or impact pulverization, or by solidifying the melt followed by griding, and mechanically mixing 0.1-50% by weight of the thus obtained powders with 50-99.9% by weight of a silver-tin-copper amalgam alloy powders in a given proportion.

(A): Silver alloy containing no less than 50 % by weight of silver and 0.01-10% by weight of selenium with or without one of more of metallic elements selected from the group consisting of gold, copper, cobalt, nickel, tin, indium, palladium, antimony, germanium and zinc, (B): Copper alloy containing no less than 50 % by weight of copper and 0.01-5% by weight of selenium with or without one or more of metallic elements selected from the group consisting of gold, silver, cobalt, nickel, tin, indium, palladium, antimony, germanium and zinc, and (C): Alloy mix of (A) and (B), wherein the total amount of silver and copper exceeds 50% by weight, and the amount of selenium is in a range of 0.01-10% by weight.

(D): The amount of the silver-tin-copper alloy powders used as (D) is in a range of 50-99.9% by weight. Mercury in an amount up to 3% may be added in advance to at least one of the any one of (A), (B) and (C). The amount of mercury is then based on the total amount of the dental formulation. As mentioned above, the purpose of the mercury addition is amalgamation.

It is noted that the objects of the present invention are also achieved by incorporating selenium into the starting alloys when mercury is added thereto for amalgamation.

The present invention will now be elucidated with reference to the following non-restrictive examples.

Example 1

A silver alloy consisting of 72% of silver, 27% of copper and 1% of selenium was melted, sprayed through a nozzle in a nitrogen stream, and passed through a 270-mesh sieve to obtain fine particles.

A silver-tin-copper amalgam alloy consisting of 70% of silver, 27% of tin and 3% of copper was then poured into a mold to prepare an ingot. The ingot was cut on a lathe, and passed through a 200-mesh sieve to obtain fine particles which were in turn subjected to a heat treatment.

40% of the first particles were mixed with 60% of the second particles to obtain alloy powders. One part by weight of the alloy powders was mechanically mixed with 1.2 parts by weight of mercury for 15 seconds by a commercially available amalgamater, for instance, GC HIMIX VS-III manufactured by GC Dental Industrial Corp. to prepare a test piece.

Example 2

A copper alloy consisting of 97% of copper and 3% of selenium was rotated and melted in an argon gas stream, the alloy was powdered by centrifugal force. The powder passed through a 270-mesh sieve to obtain fine particles.

A silver-tin-copper amalgam alloy consisting of 60% of silver, 30% of tin and 10% of copper was melted, sprayed in a nitrogen stream, and passed through a 270-mesh sieve to obtain fine particles which were in turn subjected to a heat treatment.

20% of the first particles were mechanically mixed with 80% of the second particles to obtain alloy powders. One part by weight of the alloy powders mechanically mixed with 0.9 parts by weight of mercury for 10 seconds by the amalgamater to prepare a test piece.

EXAMPLE 3

A silver alloy consisting of 90% of silver, 3% of gold and 7% of selenium was melted and poured into a mold to prepare an ingot which was then cut on a lathe and passed through a 200-mesh sieve to obtain fine particles.

A silver-tin-copper amalgam alloy consisting of 40% of silver, 30% of tin and 30% of copper was melted, sprayed in a nitrogen stream, and passed through a 270-mesh sieve to obtain fine particles which were then subjected to heat treatment.

5% of the first particles were mechanically mixed with 95 % of the second particles to obtain alloy powders. One part by weight of the alloy powders was mechanically mixed with one part by weight of mercury for 15 seconds by the amalgamater to prepare a test piece.

EXAMPLE 4

A copper alloy consisting of 79.5% of copper, 20% of nickel and 0.5% of selenium was melted, sprayed in a nitrogen stream, and passed through 270-mesh sieve to obtain fine particles.

A silver alloy consisting of 96% of silver and 4% of selenium was melted, sprayed through a nozzle in a nitrogen stream, and passed through a 270-mesh sieve to obtain fine particles.

A silver-tin-copper amalgam alloy consisting of 68% of silver, 28% of tin and 3% of copper with the balance being 1% of zinc was melted and poured into a mold to prepare an ingot which was then cut on a lathe and passed through a 200-mesh sieve to obtain fine particles, which were in turn subjected to a heat treatment.

The first, second and third particles were mechanically mixed together in a proportion of 10%, 10% and 80% to obtain alloy powders. One part by weight of the alloy powders was mechanically mixed with 1.1 parts by weight of mercury for 15 seconds by the amalgamater to obtain a test piece.

EXAMPLE 5

A copper alloy consisting of 75% of copper, 23% of cobalt and 2% of selenium was melted, sprayed throug a nozzle in a nitrogen stream, and passed through a 270-mesh sieve to obtain fine particles.

A silver-tin-copper amalgam alloy consisting of 65% of silver, 30% of tin and 5% of copper was melted, sprayed through a nozzle in a nitrogen stream, and passed through a 270-mesh sieve to obtain fine particles which were then subjected to a heat treatment.

10% of the first particles were mechanically mixed with 90% of the second particles to obtain alloy powders. One part by weight of the alloy powders was mechanically mixed with 0.85 parts by weight of mercury for 10 seconds by the amalgamater to obtain a test piece.

COMPARISON EXAMPLE 1

A silver alloy consisting of 73% of silver and 27% of copper was melted, sprayed through a nozzle in a nitrogen stream, and passed through a 270-mesh sieve to obtain fine particles.

A silver-tin-copper amalgam alloy consisting of 79% of silver, 27% of tin and 3% of copper was melted, sprayed through a nozzle in a nitrogen stream, and passed through a 270-mesh sieve to obtain fine particles which were subjected to a heat treatment.

40% of the first particles were mechanically mixed with 50% of the second particles to obtain alloy powders. One part by weight of the alloy powders was mechanically mixed with 0.85parts by weight of mercury for 10 seconds by the amalgamater to prepare a test piece.

COMPARISON EXAMPLE 2

An amalgam alloy consisting of 60% of silver, 28% of tin and 12% of copper was melted, sprayed through a nozzle in a nitrogen stream, and passed through a 270-mesh sieve to obtain alloy powders. One part of the alloy powders was mechanically mixed with 0.9 parts by weight of mercury for 10 seconds by the amalgamater to obtain a test piece.

COMPARISON EXAMPLE 3

A silver alloy consisting of 80% of silver and 20% of nickel was melted and poured into a mold to prepare an ingot which was then cut on a lathe and passed through a 200-mesh sieve to obtain fine particles.

A silver-tin-copper amalgam alloy consisting of 68% of silver, 27% of tin and 5% of copper was melted and poured into a gold cavity to prepare an ingot which was cut on a lathe and passed through a 200-mesh-sieve to obtain fine particles which were in turn subjected to heat treatment.

20 % of the first particles were mechanically mixed with 80% of the second particles to obtain alloy powders. One part by weight of the alloy powders was mechanically mixed with 1.2 parts by weight of mercury for 15 seconds to prepare a test piece.

The test pieces obtained in Examples 1–5 inclusive and Comparison Examples 1–3 inclusive were examined on their manipulation time, compressive strength and flow. The results are set forth in the following table. The manipulation time referred to in the table is defined as a period of time during which the test pieces packed in the teeth model can easily be manipulated. The compressive strength and the deformation under pressure were measured according to the American Dental Society Sepcification No. 1.

TABLE

| | Manipulation Time (min.) | Compressive Strength | | Flow (%) |
| --- | --- | --- | --- | --- |
| | | After 30 min | After 24 hours | |
| Ex. 1 | 6 | 980 | 5210 | 1.05 |
| Ex. 2 | 4 | 1510 | 5640 | 0.55 |
| Ex. 3 | 4 | 1480 | 5280 | 0.80 |
| Ex. 4 | 6 | 960 | 5190 | 1.00 |
| Ex. 5 | 6 | 1230 | 5910 | 0.30 |
| Comp. Ex. 1 | 6 | 570 | 4770 | 1.60 |
| Comp. Ex. 2 | 6 | 610 | 5010 | 0.95 |
| Comp. Ex. 3 | 4 | 1090 | 4860 | 1.90 |

From the above-mentioned results, it is found that the test pieces of Examples 1, 4 and 5 are similar in manipulation time to those of Comparison Examples 1 and 2. However, the inventive pieces have their compressive strength after 30 minutes larger than those of the comparative pieces by a factor of about 1.5. This means that the inventive pieces show improved resistance to the initial biting forces in the mouth. The inventive pieces also have improved compressive strength after 24 hours, and show limited flow. Thus, the inventive pieces provide filled and packed restorations which stand up to biting forces over an extended period of time with no substantial fear of failures. These hold for a comparison of Examples 2 and 3 with Comparison Example 3.

According to the present invention, selenium may be added alone or in the eutectic form with other metallic elements. However, preference is given to using selenium in the eutectic form, since further improvements are then introduced in compressive strength, flow and mechanical properties. In addition, uniform amalgamation proceeds rapidly in an early stage so that more stable restorations are obtained.

As explained in detail as above, the selenium-containing amalgam alloys according to the present invention show markedly improved mechanical properties after setting, inclusive of their initial compressive strength, and considerably reduce or eliminate the toxicity to cells of mercury.

The selenium-containing dental amalgam alloys can also be manufactured by the method of the present invention in an easy and effective manner.

Thus, the present invention can be a great breakthrough in the dental art.

What is claimed is:

1. Selenium-containing amalgam alloys for dental restoration comprising 0.1–50% by weight of a copper alloy powder containing no less than 50% by weight of copper and 0.01–5% by weight of selenium, mixed with 50–99.9% by weight of a silver-tin-copper amalgam alloy powder.

2. Selenium-containing amalgam alloys as in claim 1, in which said copper alloy powder contains one or more metallic elements selected from the group consisting of gold, silver, cobalt, nickel, tin indium, palladium, antimony, germanium and zinc.

3. Selenium-containing amalgam alloys as in claim 1, wherein said copper alloy powder and said silver-tin-copper amalgam alloy powder is preamalgamated with mercury in an amount of no higher than 3% by weight based on the total weight thereof.

4. Selenium-containing amalgam alloys as in claim 3, in which said copper alloy powder contains one or more metallic elements selected from the group consisting of gold, silver, cobalt, nickel, tin, indium, palladium, antimony, germanium and zinc.

* * * * *

UNITED STATES PATENT AND TRADEMARK OFFICE
CERTIFICATE OF CORRECTION

PATENT NO. : 4,528,034
DATED : July 9, 1985
INVENTOR(S) : ATSUSHIGE SATO ET AL

It is certified that error appears in the above-identified patent and that said Letters Patent is hereby corrected as shown below:

At column 5, line 58, change "79" to --70--.

At column 5, line 64, change "50" to --60--.

Signed and Sealed this

Fifth Day of November 1985

[SEAL]

Attest:

*Attesting Officer*

DONALD J. QUIGG

*Commissioner of Patents and Trademarks*